US008246605B2

(12) United States Patent
 Valaie

(10) Patent No.: US 8,246,605 B2
(45) Date of Patent: Aug. 21, 2012

(54) CLEAR FLUSH CHECK FLOW

(75) Inventor: Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 172 days.

(21) Appl. No.: 12/777,029

(22) Filed: May 10, 2010

(65) Prior Publication Data

US 2011/0275974 A1    Nov. 10, 2011

(51) Int. Cl.
 *A61M 25/16* (2006.01)
 *A61M 25/18* (2006.01)
(52) U.S. Cl. ........................................... 604/533
(58) Field of Classification Search ............... 604/167.01–167.04, 168.01, 246, 604/82, 84, 533–535, 537
 See application file for complete search history.

(56) References Cited

U.S. PATENT DOCUMENTS

| 4,610,665 | A | | 9/1986 | Matsumoto et al. | |
|---|---|---|---|---|---|
| 4,769,005 | A | * | 9/1988 | Ginsburg et al. | 604/510 |
| 4,795,439 | A | * | 1/1989 | Guest | 604/43 |
| 5,849,005 | A | | 12/1998 | Garrison et al. | |
| 6,063,060 | A | | 5/2000 | Moenning | |
| 6,394,141 | B2 | * | 5/2002 | Wages et al. | 138/115 |
| 6,416,499 | B2 | * | 7/2002 | Paul, Jr. | 604/256 |
| 7,172,580 | B2 | | 2/2007 | Hruska et al. | |
| 2003/0051735 | A1 | | 3/2003 | Pavcnik et al. | |
| 2005/0155608 | A1 | | 7/2005 | Pavcnik et al. | |
| 2006/0190005 | A1 | | 8/2006 | Kennedy, III et al. | |
| 2009/0259287 | A1 | | 10/2009 | Valaie | |

* cited by examiner

*Primary Examiner* — Christopher D Koharski
(74) *Attorney, Agent, or Firm* — Brinks Hofer Gilson & Lione

(57) ABSTRACT

A flow adapter has a housing, a connector disposed on the distal end of the housing, a valve member disposed within the housing, and a side port disposed on the housing. The housing has a first opening in a proximal end of the housing, a second opening in a distal end of the housing, and a passageway extending between the first and second openings. The first and second openings and the passageway are configured for the passage of an elongate medical device there through. The connector is in communication with the second opening and is configured for attachment to the medical introducer. The side port is fluidly connected to the passageway by one or more conduits extending along a side of the housing and the conduits are configured to direct the flushing fluid to a proximal portion of the passageway adjacent to the first opening.

13 Claims, 6 Drawing Sheets

CLEAR FLUSH CHECK FLOW

BACKGROUND

The present disclosure relates generally to a flow adapter for use with an introducer for introducing catheters and other devices for medical intervention.

Catheters have been introduced as a minimally invasive device in many medical applications for temporary catheterization such as clot aspiration and long term catheterization such as hemodialysis. Hemodialysis catheters usually stay in the subject body for extended periods of time (e.g. several weeks or more) to withdraw fluid from the body for processing and simultaneously introduce processed fluid back into the body. Although hemodialysis catheters are minimally invasive, they are foreign to the body and may cause an inflammatory reaction. The reaction may introduce thrombus around the surface of catheters especially in the hub of introducer.

A check flow with a sidearm enables catheters to be flushed with saline and clear the hub and the lumen of any blood or fluids. It is necessary to keep blood out of the catheter to prevent clotting. However, a small amount of blood is often trapped in the back portion of the hub, thereby making it necessary to leave a small amount of anti clotting medicine such as Heparin in the hub to prevent any remaining blood from clotting. In addition to dangers of blood clots, small amounts of anti clotting medicines will enter the blood stream during or after each use of the catheter and may prolong the recovery period or cause complications with patients who do not respond well to these types of drugs.

To solve these problems, the instant application provides a check valve with multiple internal flushing ports disposed about the upstream end of the valve.

SUMMARY

The present invention provides a flow adapter for use with a medical introducer for introducing catheters and other devices for medical intervention.

One embodiment of the flow adapter comprises a housing, a connector disposed on the distal end of the housing, a valve member disposed within the housing, and a side port disposed on the housing. The housing comprises a first opening in a proximal end of the housing, a second opening in a distal end of the housing, and a passageway extending between the first and second openings. The first and second openings and the passageway are configured for the passage of an elongate medical device there through. The connector disposed on the distal end of the housing is in communication with the second opening and the connector is configured for attachment to the medical introducer. The valve member disposed within the housing is configured to prevent the leakage of blood or other bodily fluids from the adapter. The side port disposed on the housing is configured to be attached to a source of flushing fluid. The side port is fluidly connected to the passageway by one or more conduits extending along a side of the housing and configured to direct the flushing fluid to a proximal portion of the passageway adjacent to the first opening.

In one embodiment, the conduits are disposed close to each other near the top inner surface of the housing. In another embodiment, the conduits are disposed with equal distance to each other around the inner surface of the housing.

In another aspect of the present invention, there is provided a method for introducing an elongate medical device through a medical introducer having a housing. The method comprises: providing a housing and an introducer, the housing comprising a first opening in the proximal end of the housing, a second opening in a distal end of the housing, and a passageway extending between the first and second openings; attaching a source of flushing fluid to a side port disposed on the housing, the side port being fluidly connected to the passageway by one or more conduits extending along a side of the housing; and passing fluid through conduits and into the passageway.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION OF THE PREFERRED EMBODIMENTS

In the present application, the term "proximal" refers to a direction that is generally toward a physician during a medical procedure, while the term "distal" refers to a direction that is generally toward a target site within a patient's anatomy during a medical procedure.

Figure 1:
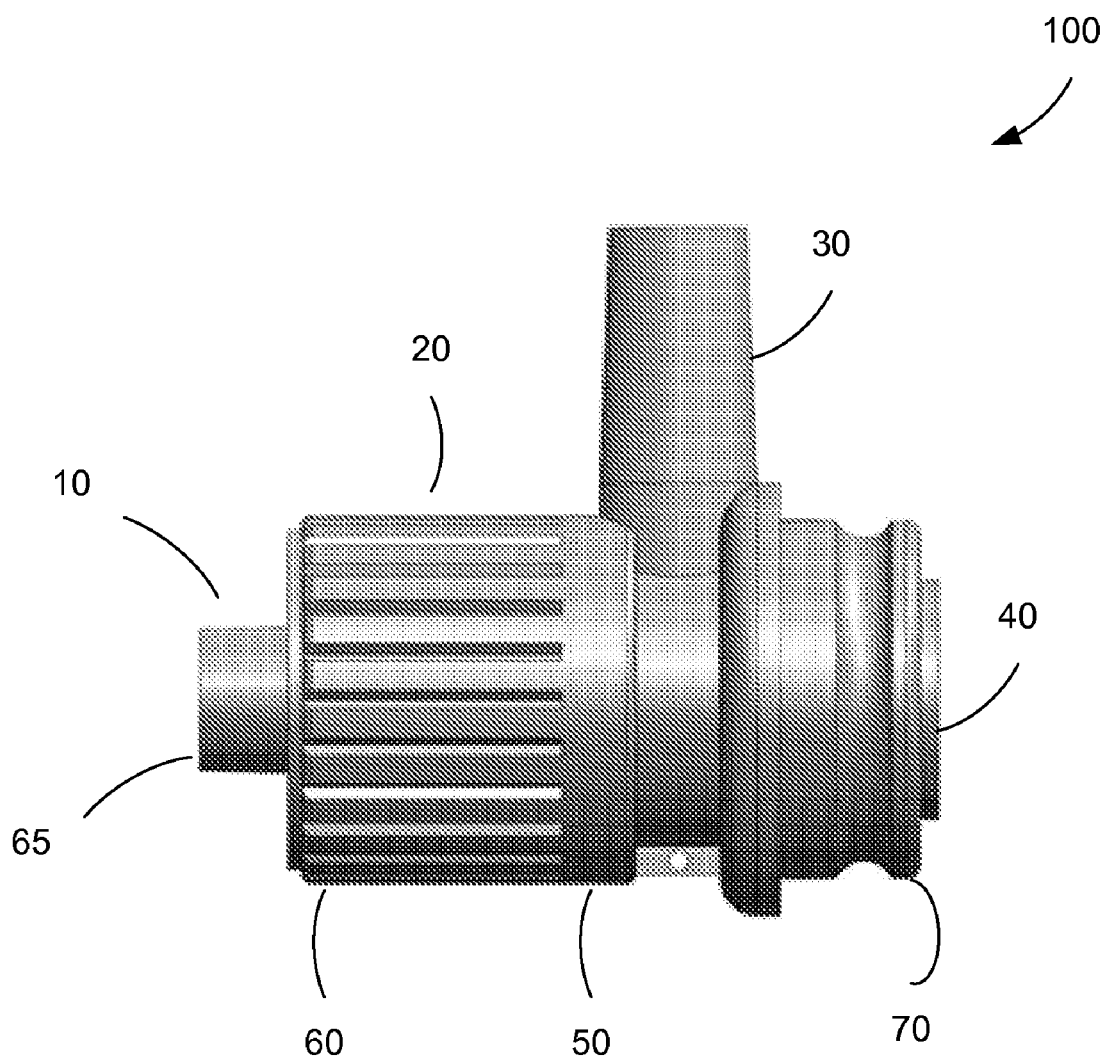
FIG. 1 is a side view of a first embodiment of medical introducer.
Figure 2:
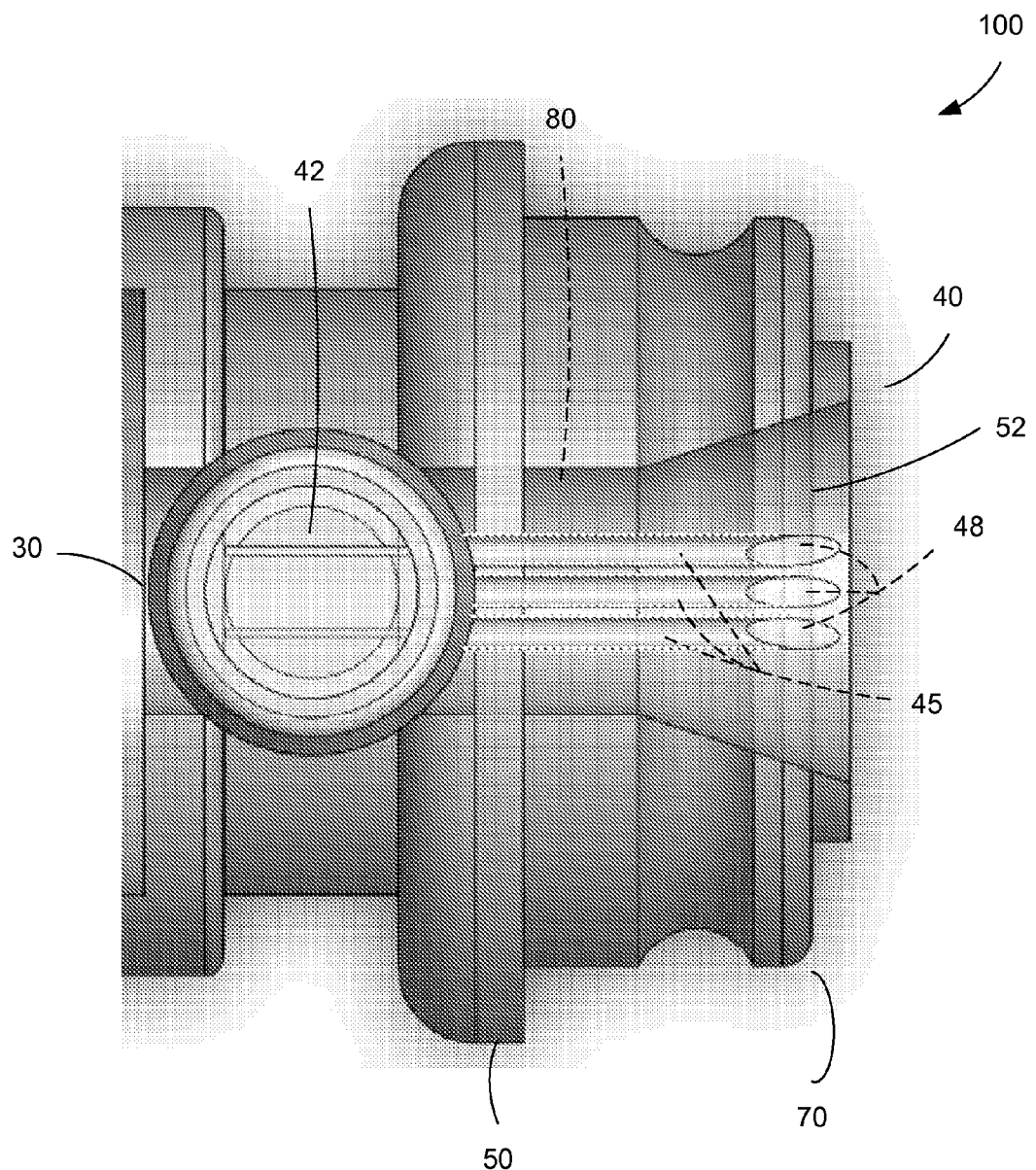
FIG. 2 is a top view of the medical introducer of FIG. 1.
Figure 3:
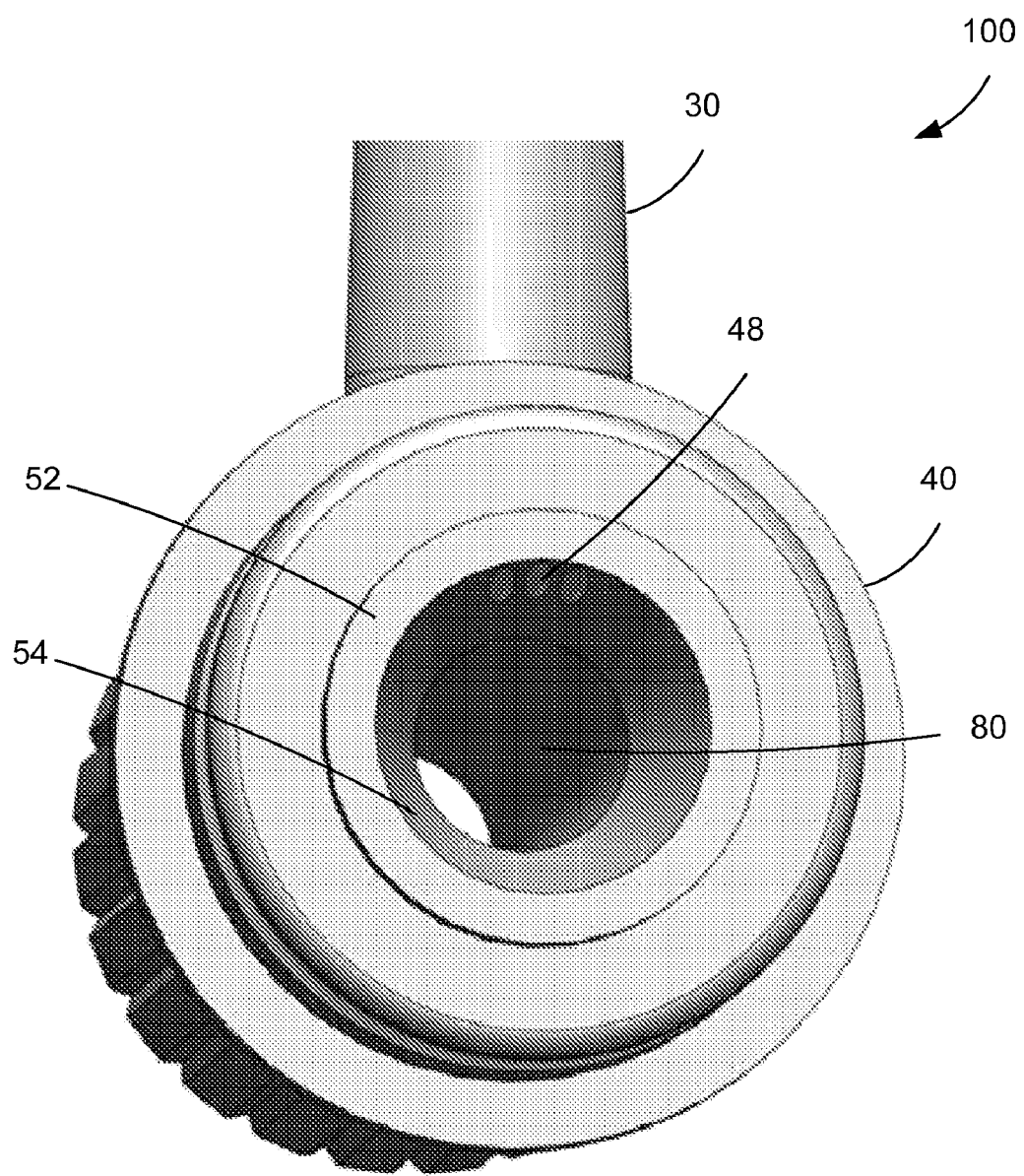
FIG. 3 is an end view of the medical introducer in FIG. 1.

Referring now to FIGS. 1-3, a first embodiment of the flow adapter 100 is disclosed. The flow adapter 100 comprises a housing 50, a connector 10 disposed on the distal end 60 of the housing 50, a valve member 20 disposed within the housing 50, and a side port 30 disposed on the housing 50. The housing 50 comprises a first opening 40 in a proximal end 70 of the housing 50, a second opening 65 in a distal end 60 of the housing 50, and a passageway 80 extending between the first and second openings 40, 65. The first and second openings 40, 65 and the passageway 80 are configured for the passage of an elongate medical device there through. The connector 10 disposed on the distal end 60 of the housing 50 is in communication with the second opening 65, the connector 10 is configured for attachment to a medical introducer. The valve member 20 disposed within the housing 50 is configured to prevent the leakage of blood from the adapter 100. The side port 30 disposed on the housing 50 is configured to be attached to a source of flushing fluid. The side port 30 is also fluidly connected to the passageway 80 by one or more conduits 42 extending along a side of the housing. The conduits 42 are configured to direct the flushing fluid to a proximal portion of the passageway 80 adjacent to the first opening 40.

As shown in FIG. 2 and FIG. 3, the one or more conduits 42 may comprise a plurality of tubes 45 disposed within a wall 52 of the housing 50. The plurality of tubes 45 each comprise a port 48 disposed on an interior wall surface 54 of the housing 50. In FIG. 2 and FIG. 3, the conduits 42 are disposed adjacent to each other and on the same side as the side port 30, i.e. the top surface as shown in FIG. 1. The ports 48 may also have openings towards the interior wall surface 54 and the proximal portion or upstream of the passageway 80. With the ports 48 at the upstream of the passageway 80, fluids can be directed to flush or remove the remaining blood clot or other bodily fluid residue.

The flow adapter 100 may be used in many applications to introduce catheters for minimally invasive surgeries or diagnoses. For example, in angioplasty, the elongate medical device to be introduced may be a balloon catheter. In a hemodialysis treatment, the elongate medical device may be a hemodialysis catheter. In some treatments or diagnosis within body lumens, the elongate medical device may be a closed end catheter. In other applications such as embolotherapy, the elongate medical device may be a non-tapered end catheter.

Figure 4:
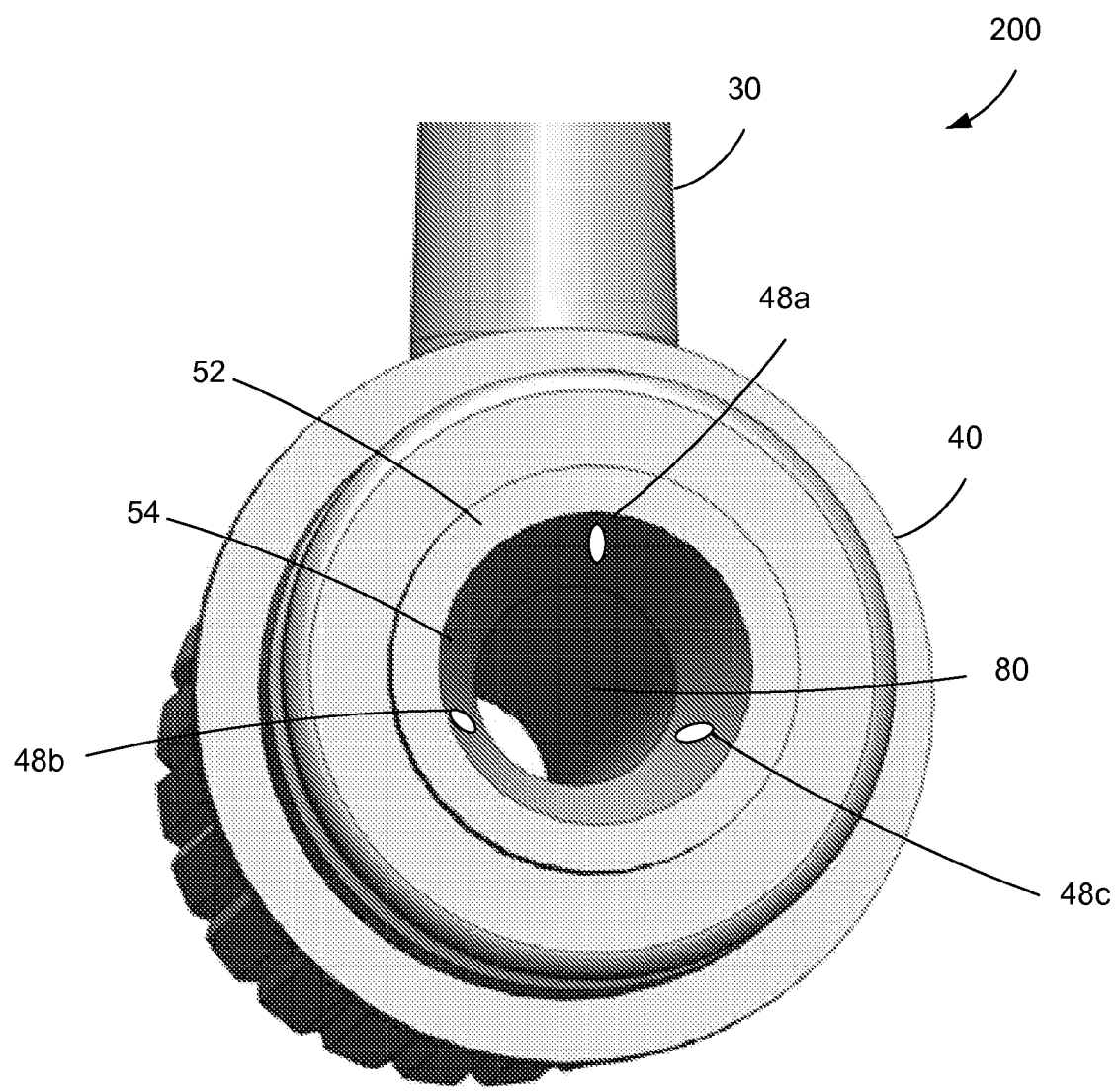
FIG. 4 is an end view of a second embodiment of a medical introducer.

A second embodiment of the flow adapter 200 is shown in FIG. 4. In the second embodiment, the one or more conduits 42 are circumferentially disposed about the interior wall surface 54 of the housing 50. Here, the distance between the ports 48*a*, 48*b*, and 48*c* are equal when there are three conduits. One of the conduits may be spirally disposed through or along the interior wall of the housing 50. It should be noted that the number of conduits may vary depend on applications. The locations of the conduits and ports may also vary depend on the specific applications.

Figure 5:
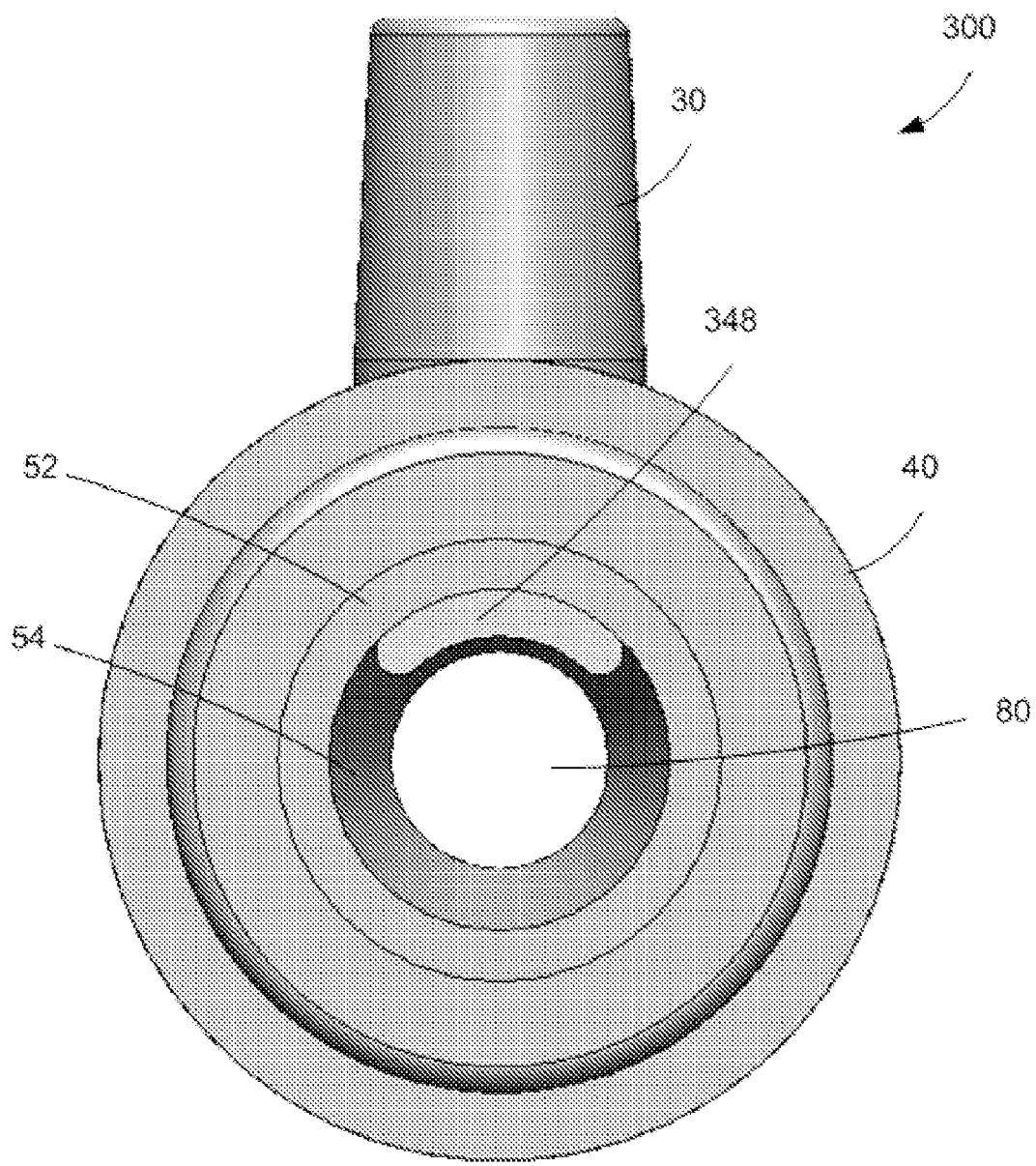
FIG. 5 is an end view of a third embodiment of a medical introducer.

A third embodiment of the flow adapter 300 is shown in FIG. 5. In this embodiment, one or more of the conduits 42 and/or the ports 348 may comprise a noncircular cross-sectional shape. For example, the conduit 42 and the port 348 of this embodiment each have a noncircular cross-sectional shape that is kidney shaped. The port 348 may thus cover a larger area compared with previously disclosed embodiments. The exact shape of the one or more conduits 42 and their ports may vary based on specific applications or the configuration of the device.

Figure 6:
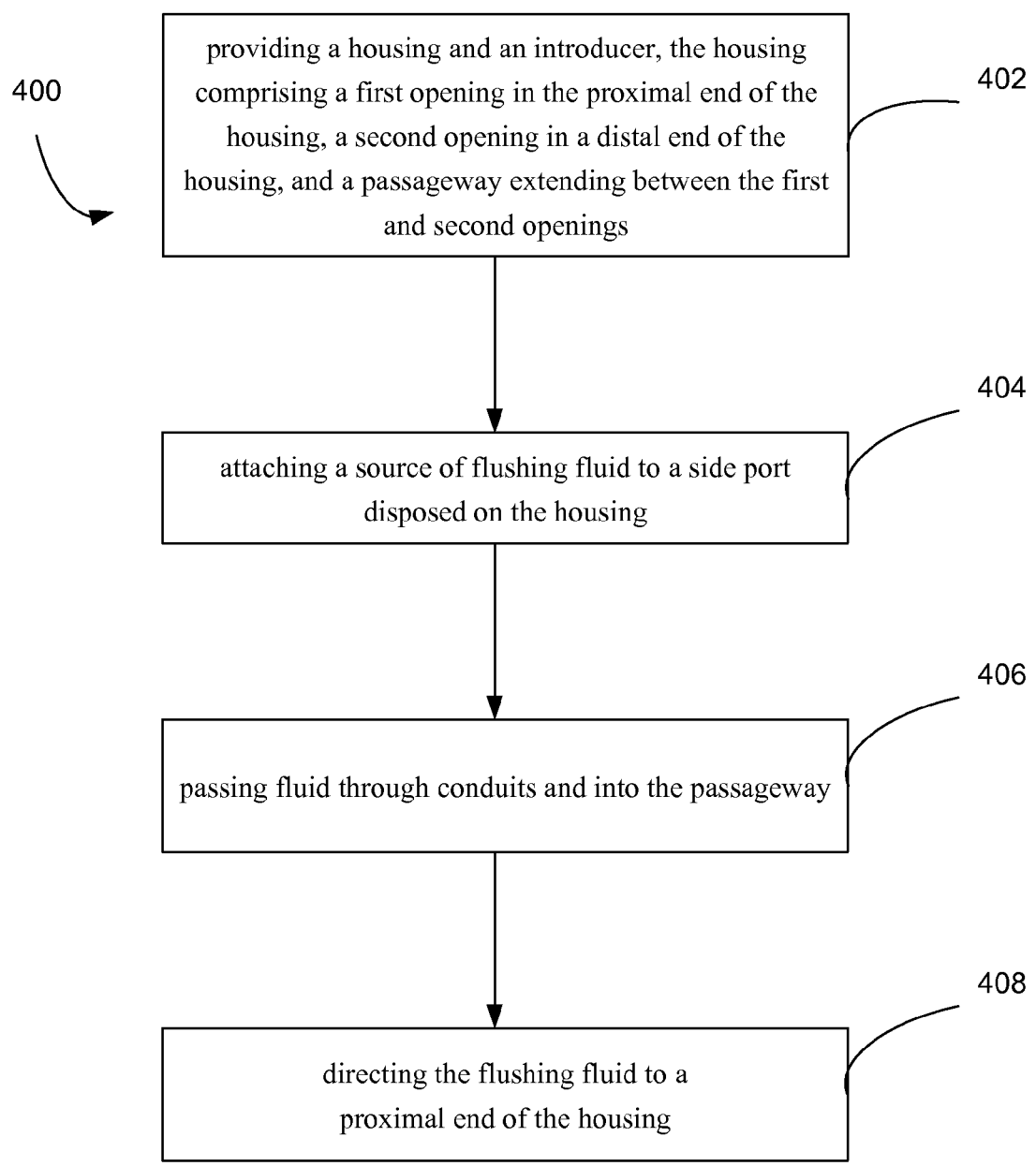
FIG. 6 is a block diagram of a method for introducing an elongate medical device through a medical introducer.

Accordingly, a method 400 for introducing an elongate medical device through the medical introducer having a housing is also shown in FIG. 6. The method 400 comprises the following steps. In step 402, providing a housing and an introducer, the housing comprising a first opening in the proximal end of the housing, a second opening in a distal end of the housing, and a passageway extending between the first and second openings. In step 404, attaching a source of flushing fluid to a side port disposed on the housing, the side port being fluidly connected to the passageway by one or more conduits extending along a side of the housing. In step 406, passing fluid through conduits and into the passageway. In step 408, the method may further comprise directing the flushing fluid to a proximal end of the housing.

Alternatively or additionally, the operator may use a computer to select an appropriate flow adapter for the medical introducer according to a table or chart stored in a computer-readable storage medium, such as Read-Only Memory (ROM), Random Access Memory (RAM), magnetic disc and compact disc.

While various embodiments of the invention have been described, it will be apparent to those of ordinary skill in the art that many more embodiments and implementations are possible within the scope of the invention. The different aspects of the described embodiments may be combined together to improve the performance of the hemodialysis catheter. Accordingly, the invention is not to be restricted except in light of the attached claims and their equivalents. Moreover, the advantages described herein are not necessarily the only advantages of the invention and it is not necessarily expected that every embodiment of the invention will achieve all of the advantaged described.

What is claimed is:

1. A flow adapter for use with a medical introducer, the adapter comprising:

a housing comprising a first opening in a proximal end of the housing, a second opening in a distal end of the housing, and a passageway extending between the first and second openings and defined by a wall of the housing, the first and second openings and the passageway each being configured for the passage of an elongate medical device there through;

a connector disposed on the distal end of the housing and in communication with the second opening, the connector configured for attachment to the medical introducer;

a valve member disposed within the housing and configured to prevent the leakage of blood from the adapter; and a side port disposed on the wall of the housing and configured to be attached to a source of flushing fluid, wherein the side port is fluidly connected to the passageway by one or more conduits extending longitudinally within the wall of the housing, the conduits configured to direct the flushing fluid to a proximal portion of the passageway adjacent to the first opening.

2. The flow adapter of claim 1, wherein the one or more conduits comprise a plurality of tubes disposed within the wall of the housing.

3. The flow adapter of claim 2, wherein the plurality of tubes each comprise at least one port disposed on an interior wall surface of the housing.

4. A flow adapter for use with a medical introducer, the adapter comprising:

a housing comprising a first opening in a proximal end of the housing, a second opening in a distal end of the housing, and a passageway extending between the first and second openings, the first and second openings and the passageway each being configured for the passage of an elongate medical device there through;

a connector disposed on the distal end of the housing and in communication with the second opening, the connector configured for attachment to the medical introducer;

a valve member disposed within the housing and configured to prevent the leakage of blood from the adapter; and a side port disposed on the housing and configured to be attached to a source of flushing fluid, wherein the side port is fluidly connected to the passageway by one or more conduits extending along a side of the housing, the conduits configured to direct the flushing fluid to a proximal portion of the passageway adjacent to the first opening;

wherein the one or more conduits comprise a plurality of tubes disposed within a wall of the housing;

wherein the plurality of tubes each comprise a port disposed on an interior wall surface of the housing, and wherein the ports are circumferentially disposed about the interior wall surface of the housing.

5. A flow adapter for use with a medical introducer, the adapter comprising:

a housing comprising a first opening in a proximal end of the housing, a second opening in a distal end of the housing, and a passageway extending between the first and second openings, the first and second openings and the passageway each being configured for the passage of an elongate medical device there through;

a connector disposed on the distal end of the housing and in communication with the second opening, the connector configured for attachment to the medical introducer;

a valve member disposed within the housing and configured to prevent the leakage of blood from the adapter; and a side port disposed on the housing and configured to be attached to a source of flushing fluid, wherein the side port is fluidly connected to the passageway by one or more conduits extending along a side of the housing, the conduits configured to direct the flushing fluid to a proximal portion of the passageway adjacent to the first opening;

wherein the one or more conduits comprise a plurality of tubes disposed within a wall of the housing;

wherein the plurality of tubes each comprise a port disposed on an interior wall surface of the housing, and wherein the ports have openings towards the interior wall surface and the proximal portion of the passageway.

6. The flow adapter of claim 1, wherein the elongate medical device is a balloon catheter.

7. The flow adapter of claim 1, wherein the elongate medical device is a hemodialysis catheter.

8. The flow adapter of claim 1, wherein the elongate medical device is a closed end catheter.

9. The flow adapter of claim 1, wherein the elongate medical device is a non-tapered end catheter.

10. The flow adapter of claim 1, wherein at least one of the one or more conduits are disposed along the surface of a wall of the housing.

11. The flow adapter of claim 1, wherein at least one of the one or more conduits are spirally disposed along the surface of a wall of the housing.

12. The flow adapter of claim 1, wherein the one or more conduits each comprise a noncircular cross sectional shape.

13. The flow adapter of claim 12, wherein the noncircular cross sectional shape is kidney shaped.

* * * * *